(12) United States Patent
Murray et al.

(10) Patent No.: US 7,244,874 B2
(45) Date of Patent: Jul. 17, 2007

(54) STEAROYL COA DESATURASE TRANSGENIC NON-HUMAN ANIMALS

(75) Inventors: James D. Murray, Davis, CA (US); Elizabeth A. Maga, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/663,454

(22) Filed: Sep. 15, 2003

(65) Prior Publication Data

US 2004/0128705 A1    Jul. 1, 2004

Related U.S. Application Data

(60) Provisional application No. 60/411,719, filed on Sep. 17, 2002.

(51) Int. Cl.
  *A01K 67/027*  (2006.01)
  *C12N 15/00*  (2006.01)
  *A23C 9/154*  (2006.01)

(52) U.S. Cl. ............................ 800/14; 800/21; 800/25; 426/580

(58) Field of Classification Search ................... 800/14, 800/21, 25; 426/580, 34, 105
See application file for complete search history.

(56) References Cited

U.S. PATENT DOCUMENTS

| 5,667,839 | A | * | 9/1997 | Berg | ........................... 426/657 |
| 5,959,171 | A | * | 9/1999 | Hyttinen et al. | ................ 800/7 |
| 5,968,809 | A | * | 10/1999 | Knutzon et al. | ......... 435/254.2 |
| 6,333,353 | B2 | | 12/2001 | Saebo et al. | |
| 6,410,761 | B1 | | 6/2002 | Saebo et al. | |
| 6,432,469 | B1 | | 8/2002 | Rummereit | |
| 6,432,684 | B1 | | 8/2002 | Mukerji et al. | |

OTHER PUBLICATIONS

Wilmut et al. "Somatic cell nuclear transfer," Nature 419:583-586, 2002.*
Humpherys et al. "Abnormal gene expression in cloned mice derived from embryonic stem cell and cumulus cell nuclei," PNAS 99(20): 12889-12894.*
Ward et al. "The ovine stearyl-coA desaturase gene: Cloning and determination of gene number within the ovine gnome," Biochemical Society Transactions 25(S673):145.*
Miyake et al. "Increased production of Apolipoprotein B-containing lipoproteins in the absence of hyperlipidemia in transgenic mice expressing cholesterol 7a-hydroxylase," J Biol Chem 276(26):23301,23311, 2001.*
Hammer et al "Spontaneous inflammatory disease in transgenic rats expressing HLA-B27 and human beta 2m: an animal model of HLA-B27-associated human disorders," Cell 63(5):1099-112, 1990.*
Cameron et al. "Recent advances in transgenic technology," Molecular Biotechnology 7:253-265, 1997.*
Cowan et al. "Targeting gene expression to endothelium in transgenic animals: a comparison of the human ICAM-2, PECAM-1 and endoglin promoters," 10:223-231, 2003.*
Kappel et al. "Regulating gene expression in transgenic animals," Current Opinion in Biotechnology 3:548-553, 1992.*
Mench JA "Ethics, animal welfare and transgenic farm animals," in Transgenic Animals in Agriculture, pp. 251-268, CABI Publishing, New York, NY, 1999.*
Mihara, 1990, J. Biochem, 108: 1022-1029.*
Kim et al., 2000, Journal of Lipid Research, 1310-1316.*
Watts and Browse, 2000, Biochemical and Biophysical Research Communications, 272: 263-269.*
Minchin et al., 2001, J. of Pharm. and Exp. Therap., 296: 1006-1012.*
Smith, 2004, Int. J. Med. Sci., 1: 76-91.*
Page et al., 1995, Transgenic Research, 4: 12-17.*
Oback and Wells, 2002, Cloning and Stem Cells, 4: 147-168.*
Campbell et al., 2005, Reprod. Dom. Anim.,40: 256-268.*
Tian et al. 2003, Reprod. Bio. & Endocrin., 98: 1-7.*
Li et al., 2003, Reprod. Bio. & Endocrin., 84: 1-6.*
McEvoy et al., 2003, Reprod. Supp., 61:167-182.*
Vogel, 2003, Science, 300: 225-227.*
Simerly et al., 2003, Science, 300: 297.*
Pereia et al., 2003, Prostaglandins, Leukotrienes, and Essential Fatty Acids, 68, 97-106.*
Shanklin et al., 1994, Biochemistry, 33: 12787-12794.*
Hammer et al., 1986, J. Anim. Sci., 63: 269-278.*
Ward et al, 1997, Biochemical Society Transactions, 25: S673, abstract No. 145.*
Medran et al., 2000, Pflugers Archive European Journal of Physiology, 439: R24.*
Maga and Murray (1995) *Bio/Technol.* 13:1452-1457.
Strittmatter et al. (1974) *Proc. Natl. Acad. Sci. USA* 71:4565-4569.
van Berkel et al. (2002) *Nat. Biotechnol,* 20: 484-487.
Horton, J.D. et al., "Activation of Cholesterol Synthesis in Preference to Fatty Acid Synthesis in Livers and Adipose Tissue of Transgenic Mice Overexpressing Sterol Regulatory Element-Binding Protein-2" Journal of Clinical Investigation, Jun. 1998, vol. 101, No. 11, pp. 2331-2339.
Shimano, H. et al., "Isoform 1c of Sterol Regulatory Element Binding Protein in Less Active Than Isoform 1a in Livers of Transgenic Mice and in Cultured Cells. Journal of Clinical Investigation" Mar. 1997, vol. 99, No. 4, pp. 846-854.

(Continued)

*Primary Examiner*—Anne M. Wehbe
*Assistant Examiner*—Joanne Hama
(74) *Attorney, Agent, or Firm*—Paula A. Borden; Bozicevic, Field & Francis LLP

(57) ABSTRACT

The present invention provides transgenic, non-human animals that include a transgene that encodes a fatty acid desaturase, e.g., stearoyl-CoA desaturase, and methods for producing such animals. The invention further provides an expression cassette that includes a coding region for a desaturase such as stearoyl-CoA desaturase, operably linked to a heterologous, tissue-specific animal cell promoter. The invention further provides methods of producing a food product, such as milk, meat, or eggs, using a subject transgenic non-human animal, as well as food products harvested from a subject transgenic non-human animal.

16 Claims, 3 Drawing Sheets

OTHER PUBLICATIONS

Shimano, H. et al., "Overproduction of Cholesterol and Fatty Acids Causes Massive Liver Enlargement in Transgenic Mice Expressing Truncated SREBP-1a" Journal of Clinical Investigation. Oct. 1996, vol. 98, No. 7 pp. 1575-1584.

Miyake, J.H. et al. "Increased Production of Apoliprotein B-Containing Lipoproteins in the Absence of Hyperlipidema in Transgenic Mice Expressing Cholesterol 7-Alpha-Hydroxylase. Journal of Biological Chemistry" Jun. 29, 2001, vol. 276, No. 26, pp. 23304-23311.

Shimomura, I et al., "Nuclear Sterol Regulatory Element-Binding Proteins Active Genes Responsible for the Entire Program of Unsaturated Fatty Acid Biosynthesis in Transgenic Mouse Liver" Journal of Biological Chemistry. Dec. 25, 2998, vol. 273, No. 63, pp. 35299-35306.

Brembeck, F.H. et al., "The Keratin 19 Promoter is Potent for Cell-Specific Targeting of Genes in Transgenic Mice" Gastroenterology. 2001, vol. 120, pp. 1720-1728.

Aihara H., et al., "The TB3 Gene Promoter Directs Intestinal Epithelial Cell-Specific Expression in Transgenic Mice" FEBS Letters. 1999, vol. 463, pp. 185-188.

* cited by examiner

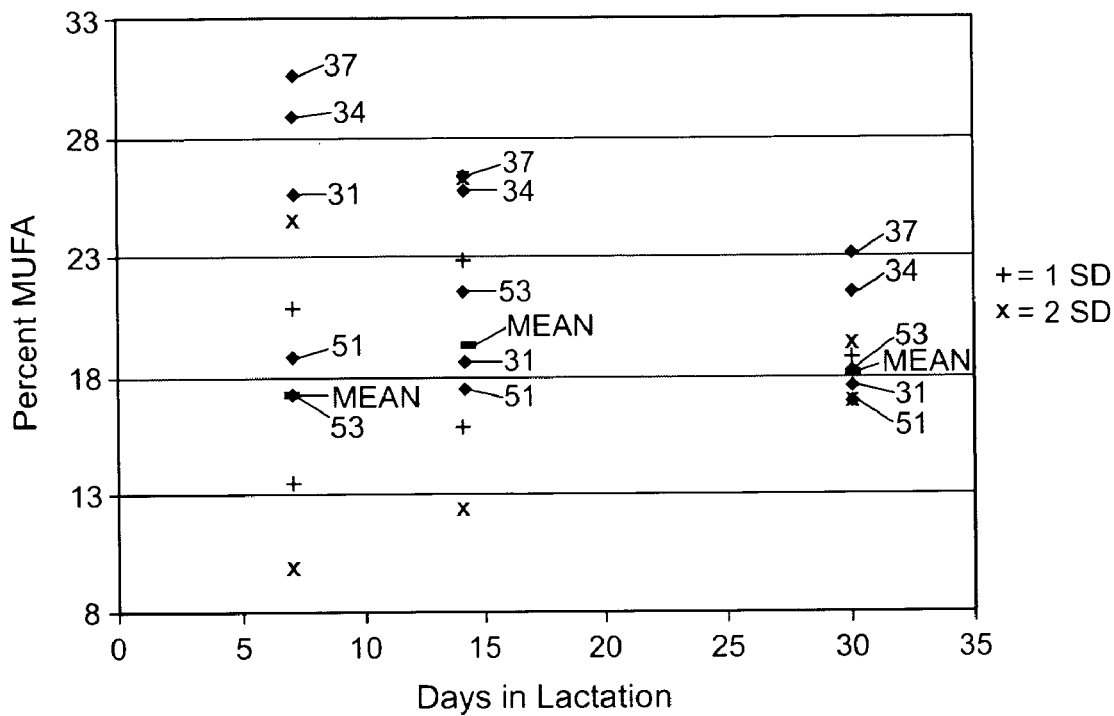
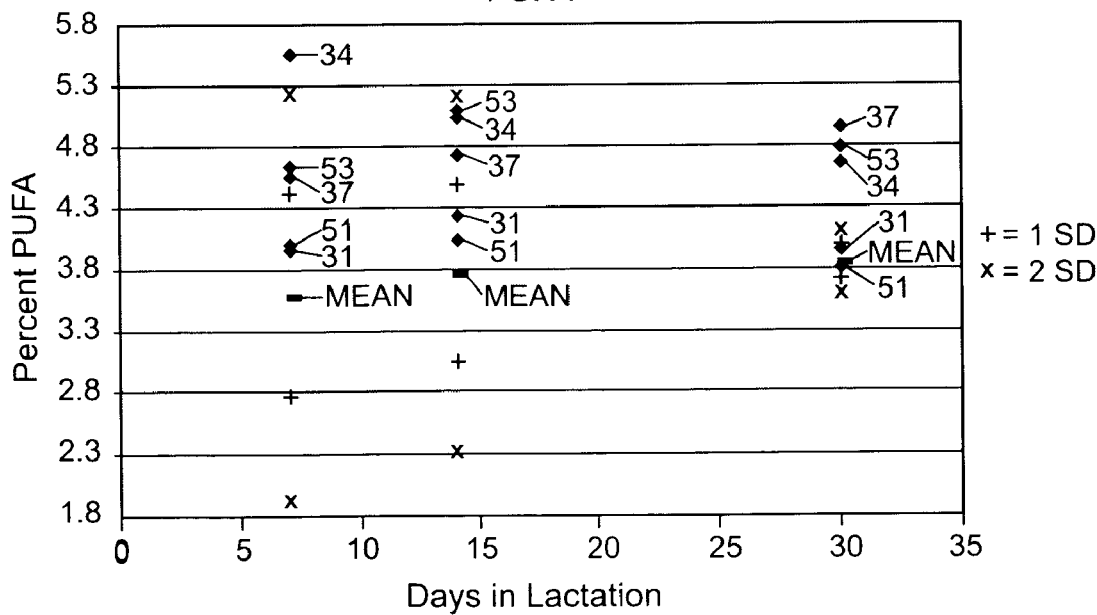

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
gaattcctta atttgcataa                                                   20

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
ctcgagcagc tgtgtcatag ttct                                              24

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
cacacagctg ctcgagatgg                                                   20

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
ctcgagtcag ctactcttgt g                                                 21
```

STEAROYL COA DESATURASE TRANSGENIC NON-HUMAN ANIMALS

CROSS-REFERENCE

This application claims the benefit of U.S. Provisional Patent Application No. 60/411,719, filed Sep. 17, 2002, which application is incorporated herein by reference in its entirety.

FIELD OF THE INVENTION

The present invention is in the field of transgenic non-human animals.

BACKGROUND OF THE INVENTION

Saturated fatty acids are long-chain aliphatic carboxylic acids with linear hydrocarbon chains having an even number of carbon atoms, usually C12-C20. Unsaturated fatty acids contain one or more double bonds, the first usually at carbon number 9. Fatty acids are stored in the form of triacylglycerols. Triacylglycerols serve three basic functions: (1) they are the storage forms of carbon and energy in adipose tissue; (2) they form lipoprotein particles which transport ingested fatty acids; and (3) they provide physical protection and thermal insulation for body organs.

Many epidemiological, clinical, and animal studies have indicated that high levels of dietary fat, especially saturated fat, lead to an increase in blood cholesterol levels and increased risk for atherosclerosis. The risk for coronary artery disease can be predicted directly from serum cholesterol levels. Saturated fatty acids are directly responsible for increasing serum cholesterol levels. A diet that minimizes cardiovascular risk factors and contributes to an overall reduction of diseases not cardiovascular in nature, such as diabetes, could be achieved by changing the dietary fat or mix of fatty acids in the diet. Plasma cholesterol levels tend to respond more to reducing saturated fatty acids than to reducing total fat intake, and plasma cholesterol reduction can be achieved with saturated fatty substituents such as monounsaturated or polyunsaturated fatty acids. Both mono- and polyunsaturated fatty acids affect cardiac risk by lowering low density lipoprotein cholesterol levels. Likewise, in many non-insulin-dependent diabetes mellitus patients, the reduction of dietary saturated fat helps lower plasma cholesterol levels and reduce the risk for coronary heart disease.

Conjugated linoleic acids (CLAs) are a group of 18 carbon FAs that have two double bonds, with positional and geometric variations around the 9, 10, 11 and 12 carbon positions. Dietarily they are principally derived from ruminant animals in meat and dairy products, as they occur only in trace amounts in plants. Considerable work has been carried out in experimental systems and animal models indicating that CLAs, principally the C 18:2 cis9 trans11 form, play a considerable role in a number of areas affecting human health. CLAs have been shown to be anti-carcinogenic and anti-athersclerosis, as well as helping to reduce severe wasting (cachexia) associated with cancer. Other studies, in a variety of animal species, have shown that CLAs can promote lean body growth, increase feed efficiency and decrease fat accumulation. Furthermore, several studies suggest that CLAs can modulate the immune response and thus reduce the cachetic response, enhance cell-mediated responses, and decrease the inflammatory response.

Approximately one third of saturated fatty acids in American diets comes from the consumption of dairy products, and approximately one quarter of saturated fatty acids in the diet are supplied by the consumption of meat. Problems associated with control of intake of saturated fatty acids include consumer compliance, with consumers generally favoring foods that have a higher content of saturated fatty acids.

There is a need in the art for food products that have lower levels of saturated fatty acids. The present invention addresses this need by providing transgenic animals that make food products (e.g., milk, meat, and eggs) having lower levels of saturated fatty acids.

Literature

U.S. Pat. No. 6,432,684; Maga and Murray (1995) *Bio/Technol.* 13:1452-1457; Strittmatter et al. (1974) *Proc. Natl. Acad. Sci. USA* 71:4565-4569; van Berkel et al. (2002) *Nat. Biotechnol.* 20:484-487; U.S. Pat. Nos. 6,432,469, 6,410,761, and 6,333,353.

SUMMARY OF THE INVENTION

The present invention provides transgenic, non-human animals that include a transgene that encodes a fatty acid desaturase, e.g., stearoyl-CoA desaturase, and methods for producing such animals. The invention further provides an expression cassette that includes a coding region for a desaturase such as stearoyl-CoA desaturase, operably linked to a heterologous, tissue-specific animal cell promoter. The invention further provides methods of producing a food product, such as milk, meat, or eggs, using a subject transgenic non-human animal, as well as food products harvested from a subject transgenic non-human animal.

Features of the Invention

The present invention features a non-human transgenic animal that includes a transgene encoding a desaturase, e.g., stearoyl-CoA desaturase. In some embodiments, the transgenic animal is a mammal. In some embodiments, the transgenic mammal is an ungulate. In other embodiments, the transgenic animal is a poultry animal. In many embodiments, the transgene is chromosomally integrated. In many embodiments, the transgene includes a coding sequence for a desaturase, such as stearoyl-CoA desaturase, operably linked to an animal tissue specific promoter. In some embodiments, the animal tissue specific promoter is a mammary specific promoter. In other embodiments, the animal tissue specific promoter is an intestinal epithelium specific promoter. In many embodiments, a tissue of a subject transgenic animal (e.g., milk, meat, or egg) has a level of saturated fatty acids (SFA) that is at least 5% lower than the level of SFA in a control non-transgenic animal of the same species.

The invention further features an expression cassette comprising a coding sequence for a stearoyl-CoA desaturase operably linked to a heterologous mammalian tissue-specific promoter. In some embodiments, the heterologous tissue specific promoter is a mammary specific promoter. In other embodiments, the heterologous tissue specific promoter is an intestinal epithelium specific promoter. In many embodiments, the expression cassette is present in a vector.

The invention further features a method for producing a non-human transgenic animal comprising a desaturase transgene, e.g., a stearoyl-CoA desaturase transgene. The method generally involves introducing a stearoyl CoA desaturase transgene into a single-celled embryo, forming a genetically modified embryo; and transferring the genetically modified embryo into a recipient female of the same species as the embryo, wherein the genetically modified embryo develops into a transgenic animal in the female. In some embodiments, the methods involve introducing a transgene into a cell, generating a genetically modified cell with a genetically modified nucleus; transferring the nucleus of the genetically modified cell into an oocyte or a single-celled embryo, generating a genetically modified oocyte or a genetically modified single-celled embryo; and transferring the genetically modified oocyte or genetically-modified single-celled embryo into a recipient female of the same species, where the genetically modified oocyte or genetically-modified single-celled embryo develops into a transgenic animal in the recipient female. In the present methods, the transgenic animal is chosen from a mouse, a rat, a rabbit, a pig, a sheep, a goat, poultry animal, and a cow. In some embodiments, the transgenic animal is a mammal, and the transgene is expressed in mammary gland cells of the mammal. In other embodiments, the transgenic animal is a mammal, and the transgene is expressed in intestinal epithelium cells of the mammal. In other embodiments, the transgenic animal is a poultry animal, and the transgene is expressed in intestinal epithelium cells of the poultry animal.

The present invention further features a method of producing a food product. In some embodiments, the method generally involves harvesting a food product from a subject non-human transgenic animal. In other embodiments, the method generally involves processing a food product harvested from a subject non-human transgenic animal.

The present invention further features a food product harvested from a subject non-human transgenic animal. In some embodiments, the food product is processed. In some embodiments, the food product is milk. In other embodiments, the food product is meat. In other embodiments, the food product is an egg. In many embodiments, the food product has from about 10 to about 67 weight percent saturated fatty acids. In many embodiments, the food product has from about 27 to about 80 weight percent monounsaturated fatty acids. In many embodiments, the food product has from about 7.5 to about 25 weight percent polyunsaturated fatty acids. In many embodiments, the food product has from about 0.400 to about 50 weight percent conjugated linoleic acid.

BRIEF DESCRIPTION OF THE DRAWINGS

FIGS. 2A-C depicts the weight percent saturated fatty acids (FIG. 2A), monounsaturated fatty acids (FIG. 2B), and polyunsaturated fatty acids (FIG. 2C) in stearoyl CoA desaturase transgenic goat milk through 30 days of lactation. The mean±one and two standard deviations for 10 controls and individual values for five stearoyl-CoA desaturase transgenic goats are shown.

DEFINITIONS

Figure 1A:
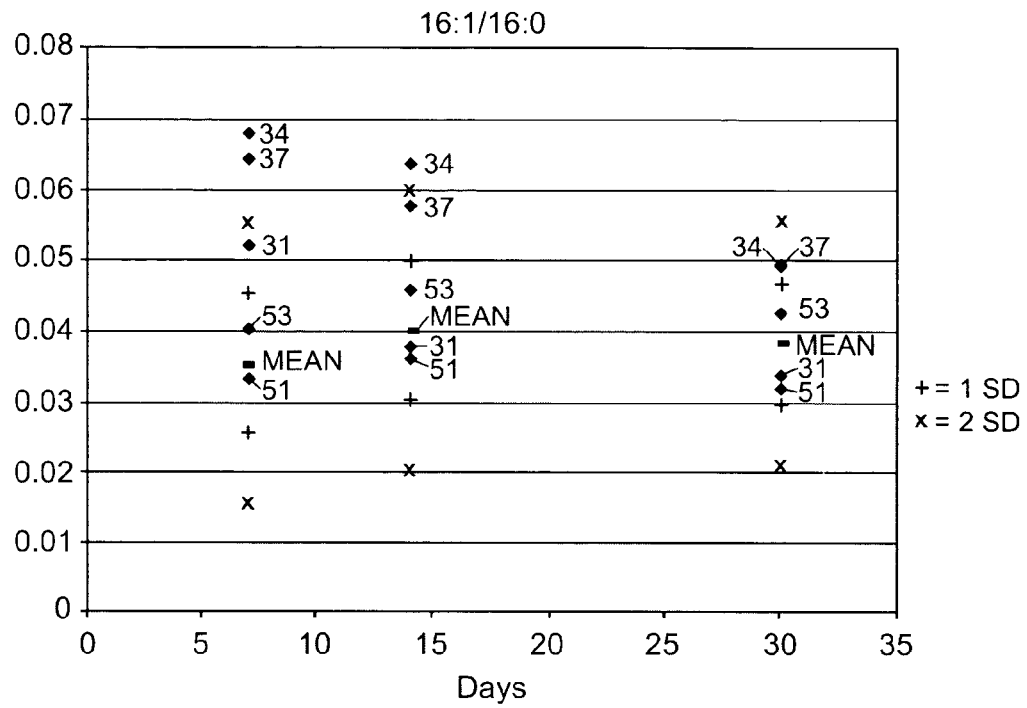
FIGS. 1A-C depict the weight percent of selected fatty acid product to precursor ratios through 30 days of lactation of stearoyl CoA desaturase transgenic goat milk and control (non-transgenic) goat milk. The mean±one and two standard deviations for 10 controls and individual values for five stearoyl CoA desaturase transgenic goats are shown.

The term "transgene" is used herein to describe genetic material which has been or is about to be artificially inserted into the genome of a non-human animal, and particularly into a cell of a living non-human mammal, or into a cell of a living bird.

The term "transformation" refers to a permanent or transient genetic change induced in a cell following the incorporation of new DNA (i.e. DNA exogenous to the cell). Where the cell is a mammalian cell or an avian cell, a permanent genetic change is generally achieved by introduction of the DNA into the genome of the cell.

The term "ES cell" as used herein refers to pluripotent embryonic stem cells and to such pluripotent cells in the very early stages of embryonic development, including but not limited to cells in the blastocyst stage of development.

The term "construct" refers to a recombinant nucleic acid, generally recombinant DNA, that has been generated for the purpose of the expression of a specific nucleotide sequence(s), or is to be used in the construction of other recombinant nucleotide sequences.

The term "operably linked" refers to a functional connection between a DNA sequence and a regulatory sequence(s), e.g., a DNA sequence and a regulatory sequence(s) are connected in such a way as to permit gene expression when the appropriate molecules (e.g., transcriptional activator proteins) are bound to the regulatory sequence(s).

The term "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein.

The term "genomic sequence" refers to a sequence having non-contiguous open reading frames, where introns interrupt the protein coding regions. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

DETAILED DESCRIPTION OF THE INVENTION

The present invention provides transgenic, non-human animals that include a transgene that encodes a fatty acid desaturase, e.g., a stearoyl-CoA desaturase (also known as "delta-9-desaturase"), and methods for producing such animals. The subject transgenic animals have reduced levels of saturated fatty acids compared to their non-transgenic counterparts and are thus useful for producing products such as milk, meat, and eggs that have reduced levels of saturated fatty acids. Food products having a reduced level of saturated fatty acids are advantageous, because consumption of such foods reduces the risks associated with a diet high in saturated fatty acids, such as an increased risk of cardiovascular disease.

Subject transgenic animals also have increased levels of conjugated linoleic acid (CLA). CLA has anticarcinogenic properties, stimulates the immune response, and reduces inflammation. CLA also increases feed efficiency and growth in farm animals fed with a diet containing a higher proportion of CLA. Products such as milk and meat produced by a subject transgenic animal contain higher levels of CLA compared with food products from non-transgenic animals of the same species. Food products from a subject transgenic animal are advantageous because consumption of such foods reduces the risk of developing cancer, enhances the immune response, and reduces inflammatory reactions. Consumption of such foods by farm animals increases the rate of growth of such animals, and increases the feed efficiency.

The subject invention also provides expression vectors that include a nucleotide sequence that encodes a fatty acid desaturase, e.g., a stearoyl CoA desaturase, and, operably linked to the coding sequence, a heterologous, animal cell tissue-specific promoter.

The subject invention further provides methods of producing a food product, by harvesting a food product, such as milk, meat, or eggs, from a subject transgenic non-human animal. The subject invention further provides foods harvested from a subject transgenic non-human animal, and food products made with such foods.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a transgenic non-human animal" includes a plurality of such animals and reference to "the transgene" includes reference to one or more transgenes and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the subject invention, the subject transgenic animals and methods for their production are described first in greater detail, followed by a review of representative applications to which the subject animals find use, e.g., in food production, etc.

Transgenic Non-Human Animals and Methods for their Production

The present invention provides transgenic non-human animals that include a desaturase transgene, e.g., a stearoyl CoA desaturase transgene. A stearoyl CoA desaturase transgene includes a nucleotide sequence that encodes stearoyl CoA desaturase. In many embodiments, the stearoyl CoA desaturase coding sequence is operably linked to a tissue-specific promoter such that the encoded stearoyl CoA desaturase is produced in a tissue-specific manner, e.g., in the mammary gland or in intestinal epithelial cells.

The description provided herein as it relates to stearoyl CoA desaturase transgenes and transgenic animals is meant to be exemplary only, and is not meant to be limited to stearoyl CoA desaturase transgenes and transgenic animals. Any desaturase transgene can be used to generate a subject transgenic animal, provided that the subject transgenic animal exhibits an altered fatty acid composition profile of those fatty acids specifically affected by the activity of the desaturase enzyme encoded by the transgene when compared to a non-transgenic littermate. For example, in many embodiments, a subject desaturase transgenic animal exhibits a reduced level of saturated fatty acids, an increased level of monounsaturated fatty acids, and an increased level of polyunsaturated fatty acids, compared to a non-transgenic littermate, as described below.

Stearoyl CoA desaturase is a membrane enzyme that converts saturated fatty acids to unsaturated fatty acids, but does not affect the production or desaturation state of most polyunsaturated fatty acids. Unsaturated fatty acids result from the addition of a cis double bond between carbons 9 and 10 to a saturated fatty acid by the action of stearoyl CoA desaturase. A subject transgenic animal that expresses a stearoyl CoA desaturase transgene therefore has a reduced level of saturated fatty acids (SFA) compared to a non-transgenic littermate. For example, the level of SFA in a subject transgenic animal, or in a component (e.g., milk, muscle tissue, or egg) of a subject transgenic animal, is at least about 2.5%, at least about 5%, at least about 10%, at least about 15%, at least about 20%, at least about 25%, at least about 30%, at least about 35%, at least about 40%, at least about 45%, or at least about 50% lower than the level in a control animal, e.g., a non-transgenic animal of the same species, such as a non-transgenic littermate. Where the component is milk, a suitable control is a female non-transgenic animal of the same species, such as a female non-transgenic littermate.

A subject transgenic animal that expresses a stearoyl CoA desaturase transgene has an increased level of monounsaturated fatty acids (MUFA), compared to a control, e.g., a non-transgenic littermate. For example, the level of MUFA in a subject transgenic animal, or in a component (e.g., milk or muscle tissue) of a subject transgenic animal, is at least about 2.5%, at least about 5%, at least about 10%, at least about 15%, at least about 20%, at least about 25%, at least about 30%, at least about 35%, at least about 40%, at least about 45%, or at least about 50% higher than the level in a control animal, e.g., a non-transgenic animal of the same species, such as a non-transgenic littermate. Where the component is milk, a suitable control is a female non-transgenic animal of the same species, such as a female non-transgenic littermate.

A subject transgenic animal that expresses a stearoyl CoA desaturase transgene has an increased level of polyunsaturated fatty acids (PUFA), compared to a control, e.g., a non-transgenic littermate. For example, the level of PUFA in a subject transgenic animal, or in a component (e.g., milk or muscle tissue) of a subject transgenic animal, is at least about 2.5%, at least about 5%, at least about 10%, at least about 15%, at least about 20%, at least about 25%, at least about 30%, at least about 35%, at least about 40%, at least about 45%, or at least about 50% higher than the level in a control animal, e.g., a non-transgenic animal of the same species, such as a non-transgenic littermate. Where the component is milk, a suitable control is a female non-transgenic animal of the same species, such as a female non-transgenic littermate.

The composition in bovine milk is typically about 70% SFA, 25% MUFA, and 5% polyunsaturated fatty acids (PUFA). The composition is generally expressed as weight percent of the total amount of SFA, MUFA, and PUFA combined, i.e., the total fatty acids.

The weight percent (e.g., weight percent of the total amount of SFA, MUFA, and PUFA combined) of SFA in a tissue (e.g., milk or muscle) of a subject transgenic animal is from about 65 to about 67.5, from about 60 to about 65, from about 55 to about 60, from about 50 to about 55, from about 45 to about 50, from about 40 to about 45, from about 35 to about 40, from about 30 to about 35, from about 25 to about 30, from about 20 to about 25, from about 15 to about 20, or from about 10 to about 15 weight percent.

Thus, e.g., the proportion (e.g., weight percent of the total amount of SFA, MUFA, and PUFA) of SFA in the milk of a subject transgenic animal that expresses a stearoyl CoA desaturase transgene under the control of a mammary gland-specific promoter is from about 65 to about 67.5, from about 60 to about 65, from about 55 to about 60, from about 50 to about 55, from about 45 to about 50, from about 40 to about 45, from about 35 to about 40, from about 30 to about 35, from about 25 to about 30, from about 20 to about 25, from about 15 to about 20, or from about 10 to about 15 weight percent.

The proportion of MUFA and PUFA is higher in a subject transgenic non-human animal, compared to a control animal, e.g., a female non-transgenic littermate. For example, the weight percent of MUFA and/or PUFA is at least about 2.5%, at least about 5%, at least about 10%, at least about 15%, at least about 20%, at least about 25%, at least about 30%, at least about 35%, at least about 40%, at least about 45%, or at least about 50% higher than the level in a control animal.

Thus, e.g., the weight percent of MUFA in a tissue (e.g., milk or muscle) of a subject transgenic animal is from about 27 to about 30, from about 30 to about 35, from about 35 to about 40, from about 40 to about 45, from about 45 to about 50, from about 50 to about 55, from about 55 to about 60, from about 60 to about 65, from about 65 to about 70, from about 70 to about 75, or from about 75 to about 80 weight percent.

Thus, e.g., the total amount of MUFA as a weight percent of the total fatty acids (where total fatty acids is the amount of SFA, MUFA, and PUFA combined) in the milk of a subject transgenic animal that expresses a stearoyl CoA desaturase transgene under the control of a mammary gland-specific promoter is from about 27 to about 30, from about 30 to about 35, from about 35 to about 40, from about 40 to about 45, from about 45 to about 50, from about 50 to about 55, from about 55 to about 60, from about 60 to about 65, from about 65 to about 70, from about 70 to about 75, or from 75 to about 80 weight percent.

The weight percent of PUFA in a tissue (e.g., milk or muscle) of a subject transgenic animal is from about 7.5 to about 10, from about 10 to about 15, from about 15 to about 20, or from about 20 to about 25 weight percent. Thus, e.g., the total amount of MUFA, as a weight percent of the total fatty acids, in the milk of a subject transgenic animal that expresses a stearoyl CoA desaturase transgene under the control of a mammary gland-specific promoter is from about 7.5 to about 10, from about 10 to about 15, from about 15 to about 20, or from about 20 to about 25 weight percent.

The weight percent of SFA in a tissue of a subject transgenic animal is reduced relative to a control animal regardless of the diet of the animal. However, a further lowering of the weight percent of SFA (and therefore a higher weight percent of PUFA and/or MUFA) is achieved in a tissue of a subject transgenic animal when the animal is fed a diet low in SFA content. Animal diets that are lower in SFA content are known in the art. See, e.g., DePeters et al. (2001) *J. Dairy Sci.* 84:929-936; Noakes et al. (1996) *Am. J. Clin. Nutr.* 63:42-46; and Grummer et al. (1991) *J. Dairy Sci.* 52:633.

A subject transgenic animal (e.g., a ruminant) has an increased level of conjugated linoleic acid (CLA; especially C18:2 cis 9 trans 11 fatty acid (also referred to herein as "rumenic acid")) compared to a control animal. The amount of CLA (and in particular of rumenic acid) in a tissue of a subject transgenic animal is at least about 2.5%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least 100%, higher than in the same tissue of a control animal. In some embodiments, the level of CLA (and in particular of rumenic acid) is about two-fold, about three-fold, about four-fold, or about five-fold higher than in the same tissue of a control animal.

Thus, e.g., where a stearoyl CoA desaturase transgene is expressed in the mammary gland, the milk produced by a subject transgenic ruminant has increased levels of CLA (and in particular of rumenic acid) compared to milk produced by a control animal, e.g., a female non-transgenic littermate. In these embodiments, the milk produced by a subject transgenic animal is at least about 2.5%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least 100%, higher than the level in the milk of a control animal. In some embodiments, the level of CLA (and in particular of rumenic acid) in the milk of a subject transgenic ruminant is about two-fold, about three-fold, about four-fold, or about five-fold higher than in the milk of a control animal.

The level of CLA can be expressed as weight percent (e.g., the amount of CLA as a percentage of total fatty acids). For example, the weight percent of CLA (and in particular of rumenic acid) in the tissue (e.g., milk or muscle) of a subject transgenic ruminant is from about 0.380 to about 4.0 weight percent, e.g., from about 0.380 to about 0.390, from about 0.390 to about 0.400, from about 0.400 to about 0.420, from about 0.420 to about 0.440, from about 0.440 to about 0.460, from about 0.460 to about 0.480, from about 0.480 to about 0.500, from about 0.500 to about 0.525, from about 0.525 to about 0.550, from about 0.550 to about 0.575, from about 0.575 to about 0.600, from about 0.650 to about 0.700, from about 0.700 to about 0.750, from about 0.750 to about 0.800 weight percent, from about 0.800 to about 0.900, from about 0.900 to about 1.0, from about 1.0 to about 1.5, from about 1.5 to about 2.0, from about 2.0 to about 2.5, from about 2.5 to about 3.0, from about 3.0 to about 3.5, or from about 3.5 to about 4.0 weight percent.

Methods of measuring levels of SFA, MUFA, PUFA, and CLAs are well known in the art, and any known method can be used to determine whether the milk or muscle tissue of a subject transgenic animal has altered levels of SFA, MUFA, and PUFA. See, e.g., "Fatty Acid and Lipid Chemistry" F. Gunstone, Blackie Academic and Professional, London, England, 1996; DePeters et al. (2001) *J. Dairy Sci.* 84:929-936; and Murray et al. (1994) *Transgenic Res.* 3:241-248.

A transgene having a coding region for stearoyl CoA desaturase is used to transform a cell, meaning that a permanent or transient genetic change, generally a permanent genetic change, is induced in a cell following incorporation of the exogenous DNA of the transgene. A permanent genetic change is generally achieved by introduction of the DNA into the genome of the cell. Vectors for stable integration include plasmids, retroviruses and other animal viruses, YACs, and the like.

Transgenic animals of the invention comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. A subject transgenic animal may be heterozygous or homozygous for the transgene. During the initial construction of the animal, "chimeras" or "chimeric animals" are generated in some methods (e.g., where ES cells are used), in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

In some embodiments, the stearoyl CoA desaturase transgene that is introduced into a cell includes an exogenous stearoyl CoA desaturase coding sequence. The exogenous gene is in some embodiments from a different species than the animal host (e.g., is a heterologous stearoyl CoA gene). The exogenous gene may or may not be altered in its coding sequence. Non-coding sequences, such as control elements, may or may not be present. Control elements, if present in the transgene, include homologous (e.g., normally associated with the coding sequence) or heterologous (e.g., not normally associated with the coding region, e.g., from another species). The introduced gene may be a wild-type gene, naturally occurring polymorphism, or a genetically manipulated sequence, for example having deletions, substitutions or insertions in the coding or non-coding regions. The stearoyl CoA desaturase coding region may be operably linked to a promoter, which may be constitutive or inducible, and other regulatory sequences required for expression in the host animal. Alternatively, the stearoyl CoA desaturase coding region may not be operably linked to a control element(s) in the transgene, but instead becomes operably linked to control element(s) when it becomes integrated into the genome. By "operably linked" is meant that a DNA sequence and a regulatory sequence(s) are connected in such a way as to permit gene expression when the appropriate molecules, e.g. transcriptional activator proteins, are bound to the regulatory sequence(s).

In other embodiments, the stearoyl CoA desaturase transgene that is introduced into a cell includes an endogenous stearoyl CoA desaturase coding sequence. In these embodiments, the coding sequence may or may not be operably linked to control element(s). The stearoyl CoA desaturase coding region may be operably linked to a promoter, which may be constitutive or inducible, and other regulatory sequences required for expression in the host animal. Alternatively, the stearoyl CoA desaturase coding region may not be operably linked to a control element(s) in the transgene, but instead becomes operably linked to control element(s) when it becomes integrated into the genome.

The transgenic animals of the present invention are other than human, including, but not limited to farm animals (pigs, goats, sheep, cows, horses (also known as ungulates or hooved animals, and including ruminants)), rodents (such as mice), poultry (e.g., avian species such as chickens, ducks, geese, turkeys, etc.), and lagomorphs (e.g., rabbits). Livestock animals such as pigs, sheep, goats and cows, (e.g., ungulates and ruminants), as well as poultry, are of particular interest.

Methods of Making a Subject Transgenic Animal

The invention provides methods of generating a subject transgenic animal. The method generally involves introducing a desaturase transgene, e.g., a stearoyl CoA desaturase transgene, into a pluripotent or totipotent cell such that the transgene is integrated into the genome of the cell, and transferring the cell into an oviduct of a synchronized recipient female of the same species as the cell.

In some embodiments, a subject transgenic animal is produced by introducing into a single cell embryo a polynucleotide that comprises a nucleotide sequence that encodes stearoyl CoA desaturase, or fragments or variants thereof, in a manner such that the polynucleotide is stably integrated into the DNA of germ line cells of the mature animal, and is inherited in normal Mendelian fashion. In accordance with the invention, a polynucleotide can be introduced into an embryo by a variety of means to produce transgenic animals. For instance, totipotent or pluripotent stem cells, zygotes (fertilized oocytes), embryonic cells, or somatic cells can be transformed by microinjection, calcium phosphate mediated precipitation, liposome fusion, electroporation, retroviral infection or by other means. Where the transformed cell is other than a zygote or embryonic cell, the transformed cells can then be introduced into embryos and incorporated therein to form transgenic animals.

In many embodiments, a polynucleotide is injected into an embryo, e.g., at the single-cell stage, forming a genetically modified embryo, and the genetically modified embryo is allowed to develop into a mature transgenic animal.

In some embodiments, the transgene is introduced into a somatic cell, where the transgene is integrated into the genome, forming a genetically modified somatic cell, and the nucleus of the genetically modified somatic cell is transferred into a single-cell embryo, forming a genetically modified embryo. The genetically modified single-cell embryo is then transferred into an oviduct of a recipient female, and the embryo allowed to develop into a mature transgenic animal.

Any method of making transgenic animals can be used as described, for example, in *Transgenic Animal Generation and Use* L. M. Houdebine, Harwood Academic Press, 1997; *Transgenesis Techniques: Principles and Protocols* D. Murphy and D. A. Carter, ed. (June 1993) Humana Press; *Transgenic Animal Technology: A Laboratory Handbook* C. A. Pinkert, ed. (January 1994) Academic Press; *Transgenic Animals* F. Grosveld and G Kollias, eds. (July 1992) Academic Press; and *Embryonal Stem Cells: Introducing Planned Changes into the Animal Germline* M. L. Hooper (January 1993) Gordon & Breach Science Pub; U.S. Pat. No. 6,344,596; U.S. Pat. No. 6,271,436; U.S. Pat. No. 6,218,596; and U.S. Pat. No. 6,204,431; Maga and Murray (1995) *Bio/Technol.* 13:1452-1457; Ebert et al. (1991) *Bio/Technol.*

9:835-838; Velander et al. (1992) *Proc. Natl. Acad. Sci. USA* 89:12003-12007; Wright et al. (1991) *Bio/Technol.* 9:830-834.

Transgenic animals also can be generated using methods of nuclear transfer or cloning using embryonic or adult cell lines as described for example in Campbell et al. (1996) *Nature* 380: 64-66; and Wilmut et al. (1997) *Nature* 385: 810-813. Cytoplasmic injection of DNA can be used, as described in U.S. Pat. No. 5,523,222. Subject transgenic animals can be obtained by introducing a construct comprising stearoyl CoA desaturase-encoding sequences.

Transgenic animals also include somatic transgenic animals, e.g., transgenic animals that include a transgene in somatic cells (and not in germ line cells). For example, the mammary gland cells of an animal are transformed with a stearoyl CoA desaturase transgene, and the transgene is expressed in mammary cells of the animal. Methods of somatic cell transformation are described in the art. See, e.g., Furth et al. (1995) *Mol. Biotechnol.* 4:121-127.

Methods for making transgenic goats are known in the art. See, e.g., Zou et al. (2002) *Mol. Reprod. Dev.* 61:164-172; Baldassare et al. (2002) *Theriogenol.* 57:275-284; and Ko et al. (2000) *Transgenic Res.* 9:215-222. Methods for making transgenic goats are also described in the Examples. Methods for making transgenic cows are known in the art, and are described in, e.g., van Berkel et al. (2002) *Nat. Biotechnol.* 20:484-487.

Methods for making transgenic pigs are known in the art. See, e.g., U.S. Pat. Nos. 6,344,596; 6,262,336; and 6,218,596.

Methods for making transgenic chickens are known in the art. See, e.g., Harvey et al. (2002) *Nat. Biotechnol.* 20:396-399; Takami et al. (2002) *Biochem. Biophys. Res. Comm.* 292:88-93; Harvey et al. (2002) *Poultry Sci* 81:202-212. Generally, the method involves introducing a stearoyl CoA transgene into a chicken embryo, where the transgene is in an avian retroviral construct, or other suitable construct.

Expression Vectors and Transgenes

A subject transgenic animal is typically generated by a method involving introducing into a cell a construct comprising a nucleotide sequence encoding a desaturase, e.g., stearoyl CoA desaturase. A "stearoyl CoA desaturase transgene" includes, at a minimum, a coding region for stearoyl CoA desaturase. In some embodiments, the nucleotide sequence encoding stearoyl CoA desaturase is operably linked to a promoter and, optionally, additional control elements, that provide for tissue-specific expression of the transgene in the animal. In other embodiments, the nucleotide sequence encoding stearoyl CoA desaturase is not operably linked to any control elements. Instead, the stearoyl CoA desaturase transgene includes, on the 5' and 3' ends of the coding region, sequences that provide for homologous recombination with an endogenous gene.

As discussed above, any nucleotide sequence that codes for a desaturase can be used to make a subject transgenic animal, including a desaturase coding sequence from rat, mouse, human, cow, goat, sheep, chicken, etc., or variant sequences that encode a desaturase. Suitable desaturase coding sequences include those coding for a delta 5 desaturase, a delta 6 desaturase, and the like. Non-limiting examples of such coding sequences are found under the following GenBank Accession numbers: human fatty acid desaturase 3 mRNA: NM_021727; human fatty acid desaturase 2 mRNA: NM_004265; human fatty acid desaturase 1 mRNA: NM_013402; mouse fatty acid desaturase 3: NM_021890; mouse fatty acid desaturase 2: NM_019699; rat fatty acid desaturase 2: NM_031344; and rat fatty acid desaturase 1: NM_053445. Plant fatty acid desaturase coding sequences can also be used. Non-limiting examples of stearoyl CoA desaturase coding sequences are provided below.

Sequences that vary from a known coding sequence for a given desaturase can be used, as long as the encoded desaturase has substantially the same activity in modifying saturated fatty acids. For example, the encoded desaturase can include one or more conservative amino acid substitutions compared to the amino acid sequence of a known desaturase. Non-limiting examples of conservative amino acid substitutions are Phe/Tyr; Ala/Val; Leu/Ile; Arg/His; Ser/Thr; etc. The encoded desaturase can also include insertions or deletions (including truncations) of one or more amino acid residues, compared to the amino acid sequence of a known desaturase. Further, the encoded desaturase can include one or more naturally occurring polymorphisms. The desaturase coding sequence can be completely or partially synthetic. A desaturase coding sequence can also be a consensus sequence, derived, e.g., by comparing the desaturase coding sequences from two or more species, and deriving therefrom a consensus sequence, using standard methods. s Any known coding sequence for stearoyl CoA desaturase can be used to make a subject transgenic animal, including a stearoyl CoA desaturase coding sequence from rat, mouse, human, cow, goat, sheep, etc. The coding sequence can be a cDNA sequence, or a genomic sequence. The coding sequence for the stearoyl CoA desaturase may be, but need not be, from the same species as the transgenic animal.

The nucleotide sequences of mRNAs encoding stearoyl CoA desaturase from a variety of animal species are known. Exemplary sequences are found under the following GenBank Accession numbers: mouse stearoyl CoA desaturase mRNA sequences: AF509570, AF609567, NM_009127, NM_009128, and NM_024450; rat stearoyl CoA desaturase mRNA sequences: AF509568, AF509569, and NM_031841; human stearoyl CoA desaturase mRNA sequence: NM_005063; goat stearoyl CoA desaturase mRNA sequence: AF325499; cow stearoyl CoA desaturase mRNA sequence: AF188710; sheep stearoyl CoA desaturase mRNA sequence: AJ001048.

In addition, sequences that vary from a known coding sequence for stearoyl CoA desaturase can be used, as long as the encoded stearoyl CoA desaturase has substantially the same activity in modifying saturated fatty acids. For example, the encoded stearoyl CoA desaturase can include one or more conservative amino acid substitutions compared to the amino acid sequence of a known stearoyl CoA desaturase. Examples of conservative amino acid substitutions are Phe/Tyr; Ala/Val; Leu/Ile; Arg/His; Ser/Thr; etc. The encoded stearoyl CoA desaturase can also include insertions or deletions (including truncations) of one or more amino acid residues, compared to the amino acid sequence of a known stearoyl CoA desaturase. Further, the encoded stearoyl CoA desaturase can include one or more naturally occurring polymorphisms.

A suitable nucleotide sequence encoding a stearoyl CoA desaturase generally has aa least about 75%, at least about 80%, at least about 85%, at least about 90%, at least about 95%, or at least about 98%, or higher, nucleotide sequence identity with a known coding sequence for stearoyl CoA desaturase. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403-10 (using default settings).

Also suitable for use are stearoyl CoA desaturase coding sequences that hybridize under stringent hybridization conditions to a known stearoyl CoA desaturase coding sequence. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 1×SSC (150 mM NaCl, 15 mM sodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C. For example, high stringency conditions include aqueous hybridization (e.g., free of formamide) in 6×SSC (where 20×SSC contains 3.0 M NaCl and 0.3 M sodium citrate), 1% sodium dodecyl sulfate (SDS) at 65° C. for about 8 hours (or more), followed by one or more washes in 0.2×SSC, 0.1% SDS at 65° C. For example, moderate stringency conditions include aqueous hybridization (e.g., free of formamide) in 6×SSC, 1% SDS at 65° C. for about 8 hours (or more), followed by one or more washes in 2×SSC, 0.1% SDS at room temperature.

As noted above, in some embodiments, a stearoyl CoA desaturase transgene includes a coding sequence for stearoyl CoA desaturase operably linked to one or more control sequences, e.g., promoters, 3' transcriptional control sequences, translational control elements, etc.

In many embodiments, a stearoyl CoA desaturase transgene includes a coding region for stearoyl CoA desaturase operably linked to one or more tissue-specific control elements, e.g., a tissue-specific promoter, and optionally additional tissue-specific control elements (e.g., a 3' untranslated region, an enhancer, and the like). The tissue-specific control element(s) can be heterologous, e.g., not normally operably linked to a stearoyl CoA desaturase coding sequence in nature, or homologous, e.g., normally operably linked to a stearoyl CoA desaturase coding sequence in nature. Tissue-specific control elements provide for expression of the stearoyl CoA desaturase transgene preferentially in a given tissue, e.g., such control elements are more active (e.g., 2-fold, 5-fold, 10-fold, 20-fold, or 50-fold more active, or greater than 50-fold more active) in a given tissue than in other tissues under normal physiological conditions. A wide variety of tissue-specific promoters are known in the art.

Promoters useful for production of stearoyl CoA desaturase in the milk of a subject transgenic animal are active in mammary tissue, e.g., the promoters are more active in mammary tissue than in other tissues under physiological conditions in which milk is synthesized. Suitable promoters provide for both specific and efficient transcription in mammary tissue. Mammary gland-specific promoters are strong promoters in mammary tissue that can support the synthesis of large amounts of protein for secretion into milk. Mammary gland-specific promoters include, but are not limited to, a whey acidic protein (WAP) promoter; αS1 casein, αS2 casein, β casein, and kappa casein promoters; an α-lactalbumin promoter; a lactoferrin promoter; and a β-lactoglobulin ("BLG") promoter. The sequences of a number of mammary gland-specific promoters have been isolated and their nucleotide sequences have been published. See, for example, Clark et al. (1987) *TIBTECH* 5:20; and Henninghausen (1990) *Protein Expression and Purification* 41:3.

Where the control element operably linked to the stearoyl CoA desaturase coding region in the transgene is a stearoyl CoA desaturase control element, the stearoyl CoA desaturase control element may be altered to provide for increased transcription, increased mRNA stability, and the like, e.g., using random or site-specific mutagenesis techniques. Methods for random and site-specific mutagenesis are well known in the art. Whether a given mutation of a control element increases the level of stearoyl CoA desaturase mRNA is readily determined using well-known methods. For example, a an expression vector that includes a stearoyl CoA desaturase promoter operably linked to a reporter gene, e.g., a nucleotide sequence encoding a detectable protein, such as a luciferase-encoding sequence, is introduced into a eukaryotic cell, and the promoter activity is determined by measuring the level of luciferase produced in the cell.

Tissue-specific promoters that are useful for altering the fatty acid content of meat (muscle tissue) include promoters that provide for specific expression in epithelial cells of the rumen and/or small intestine. Triacylglycerols are packaged into the chylomicrons that transport fatty acids to the muscle in epithelial enterocytes of the small intestine. Thus, expression of stearoyl CoA desaturase in intestinal epithelial cells changes the composition of the fatty acids that are transported to the muscle, which in turn alters the fatty acid composition of the muscle tissue.

Suitable intestinal epithelial cell-specific promoters include, but are not limited to, a T3(b) gene promoter (Aihara et al. (1999) *FEBS Lett.* 463:185-188); a villin gene promoter (Pinto et al. (1999) *J. Biol. Chem.* 274:6476-6482); a keratin 19 gene promoter (Brembeck et al. (2001) *Gastroenterol.* 120:1720-1728); a calbindin-D9K gene promoter (Colnot et al. (1998) *J. Biol. Chem.* 273:31939-31946); a lactase gene promoter (Lee et al. (2002) *J. Biol. Chem.* 277:13099-13105); and an intestinal fatty acid binding protein promoter (Sweetser et al. (1988) *Proc. Natl. Acad. Sci. USA* 85:9611-9615); and the like.

In some embodiments, a stearoyl CoA desaturase transgene will include a control element that provides for increased mRNA stability. For example, a stearoyl CoA desaturase transgene can include all or part of a 3' untranslated region (UTR) from a stearoyl CoA desaturase gene. For example, from about 50 contiguous base pairs to about 3 contiguous kilobase pairs of stearoyl CoA desaturase 3' UTR are included in the transgene, e.g., from about 50 bp to about 100 bp, from about 100 bp to about 200 bp, from about 200 bp to about 500 bp, from about 500 bp to about 1000 bp, from about 1 kb to about 1.25 kb, from about 1.25 kb to about 1.5 kb, from about 1.5 kb to about 2 kb, from about 2 kb to about 2.5 kb, or from about 2.5 kb to about 3 kb of stearoyl CoA desaturase 3' UTR is included in the transgene.

Where the transgenic animal expresses the stearoyl CoA desaturase transgene in all tissues, a strong constitutive, or an inducible promoter, is used. Strong constitutive promoters include, but are not limited to, strong promoters active in eukaryotic cells, including a promoter from cytomegalovirus (CMV), mouse mammary tumor virus (MMTV), Rous sarcoma virus (RSV), or adenovirus. Exemplary promoters include the promoter from the immediate early gene of human CMV (Boshart et al., *Cell* 41:521-530, 1985); the promoter from the long terminal repeat (LTR) of RSV (Gorman et al. (1982 *Proc. Natl. Acad. Sci. USA* 79:6777-6781); SV40 early promoter; and the adenovirus major late promoter. Such promoters are of particular interest where the transgenic animal is a transgenic poultry.

In some embodiments, a stearoyl CoA desaturase transgene is not operably linked to a control element. Instead, the transgene includes sequences that provide for homologous recombination with an endogenous gene, such that the stearoyl CoA desaturase coding sequence replaces all or part of endogenous coding sequence, and the integrated stearoyl CoA desaturase coding region is under transcriptional control of endogenous control element(s). For example, a stearoyl CoA desaturase transgene includes 5' and 3' flanking sequences that are homologous to sequences in the 5' and 3' regions of a β-lactoglobulin gene, such that the transgene integrates into the genome of a cell by homologous recombination, whereby the stearoyl CoA desaturase coding sequences of the transgene replace the endogenous β-lactoglobulin gene, and the stearoyl CoA desaturase coding sequence integrates into the genome and is under the transcriptional control of the endogenous β-lactoglobulin control elements. Methods for carrying out homologous recombination are well known in the art.

A stearoyl CoA desaturase transgene is generally provided as part of a vector (e.g., a stearoyl CoA desaturase construct), a wide variety of which are known in the art and need not be elaborated upon herein. Vectors include, but are not limited to, plasmids; cosmids; viral vectors; artificial chromosomes (HACs, YACs, BACs, etc.); mini-chromosomes; and the like. Vectors are amply described in numerous publications well known to those in the art, including, e.g., Short Protocols in Molecular Biology, (1999) F. Ausubel, et al., eds., Wiley & Sons. Vectors may provide for expression of the subject nucleic acids, may provide for propagating the subject nucleic acids, or both.

For expression, e.g., where the transgene includes a promoter, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a gene encoding the subject peptides, or may be derived from exogenous sources.

Where the transgene includes a promoter, an expression vector will generally have convenient restriction sites located near the promoter sequence to provide for the insertion of nucleic acid sequences encoding stearoyl CoA desaturase. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region.

Utility

The subject transgenic animals find use in a variety of applications, including, but not limited to, food production, research, and the like. For example, the subject animals find use in producing food products that are lower in SFA than those produced naturally. The subject animals find use in research, to analyze the effects of stearoyl CoA desaturase synthesis in various tissues.

Food Applications

The present invention provides methods for producing food products from a subject transgenic animal, and food products harvested from a subject transgenic animal. The methods generally involve harvesting a food product from a subject transgenic animal. Where the food product requires further processing, the methods involve harvesting a food product from a subject transgenic animal, and processing the food product. Thus, the invention provides a method of producing a processed food product, involving processing a food product harvested from a subject transgenic animal. The invention further provides a processed food product obtained by processing a food product harvested from a subject transgenic animal.

Methods of harvesting food products from a subject transgenic animal are well known to those in the agricultural and food production industries. Where a subject transgenic animal expresses the stearoyl CoA desaturase transgene in milk, the milk is harvested by the usual means. Where a subject transgenic animal expresses the stearoyl CoA desaturase transgene in epithelial cells of the intestine and/or rumen, meat (muscle tissue) is harvested by standard abattoir methods. Where the subject transgenic animal is a transgenic poultry, and the food product is an egg, eggs are harvested in the usual manner. Methods of processing a food product harvested from a subject transgenic animal are standard in the food processing art and are well known to those in the field.

The present invention further provides food products produced by a subject transgenic animal, and processed food products made with such food products. A subject food product includes a food product that contains a meat, egg, or milk product of a subject transgenic animal. Food products include any preparation for human consumption including for enteral or parenteral consumption, which when taken into the body (a) serve to nourish or build up tissues or supply energy and/or (b) maintain, restore or support adequate nutritional status or metabolic function.

Where a subject transgenic animal expresses the stearoyl CoA desaturase transgene in milk, food products include milk, and any food products made from or containing milk, including, but not limited to, cheese, yogurt, butter, ice cream, and other frozen desserts, whipped toppings, cream, custard, pudding, nutritional drinks, infant formula, and chocolate.

Where a subject transgenic animal expresses the stearoyl CoA desaturase transgene in epithelial cells of the intestine and/or rumen, food products include meat, meat products, and food products containing meat. Meats include beef, veal, pork, mutton, lamb, goat meat, and the like. Meat products include processed meats such as bologna, sausages, salami, and the like.

Where a subject transgenic animal is a poultry animal, food products include eggs, and food products made from or containing eggs or a portion of an egg (e.g., egg yolk, egg white); and poultry meat.

Food products of the invention are suitable for consumption by any individual. As used herein, the term "individual" includes human and non-human individuals. Non-human individuals include animals, particularly mammals, e.g., farm animals, pets, etc. The lower levels of SFA in a subject food product make the subject food products suitable for general consumption by human and non-human animal consumers. In particular, the lower levels of SFA in a subject food product make the subject food products particularly suitable for individuals who have, or are at risk for developing, a cardiovascular disease. Individuals who may have a particular interest in consuming a food product of the invention include individuals who have been diagnosed as having a cardiovascular disease; individual who are at risk of developing a cardiovascular disease; individuals who have Type I or Type II diabetes; individuals with higher than normal serum cholesterol levels; obese individuals (e.g., individuals with a body mass index (BMI; expressed as weight in kilograms divided by height, in meters, squared, or $kg/m^2$) of 30.0 or higher); overweight individuals (e.g., individuals with a BMI of between 25.0 and 29.9); individuals who have suffered one or more cardiac events; individuals who have suffered one or more strokes; hypertensive individuals; and the like. Cardiovascular diseases include, but are not limited to, atherosclerosis and coronary artery disease.

A variety of beneficial effects are attributed to CLAs, including anti-carcinogenic activity, anti-atherosclerotic activity, enhanced cell-mediated immune response, reduced cachexia, and reduced inflammatory response. See, e.g., Parodi (1999) *J. Dairy Sci.* 82:1339-1349; Pariza et al. (1999) *Toxicol. Sci.* 52:107-110; and Whigham et al. (2000) *Pharmacol. Res.* 42:503-510. Thus, a subject food product has one or more of the following attributes: a) has anti-carcinogenic properties; b) has anti-artherosclerotic properties; c) enhances cell-mediated immune responses; d) reduces cachexia; and e) reduces the inflammatory response. The increased levels of CLA (and in particular of rumenic acid) in a subject food product are of interest for consumption by all individuals. The increased levels of CLA (and in particular of rumenic acid) in a subject food product make the subject food products of particular interest for consumption by individuals whose immune systems are weakened (e.g., by disease, by bacterial infection, by radiation, by chemotherapy, or genetically); individuals who are at risk for atherosclerosis or who have been diagnosed with atherosclerosis; individuals who have cancer; etc.

CLAs also increase the growth rate of farm animals fed with a diet that includes CLAs. Thus, a subject food product increases the growth rate and feed efficiency of a farm animal fed with a subject food product. Thus, a subject food product is of particular interest for feeding a farm animal (e.g., a pig, a cow, a goat, etc.).

The level of SFA in a subject food product (e.g., milk, meat, or egg, or milk-, meat-, or egg-containing food product) is at least about 2.5%, at least about 5%, at least about 10%, at least about 15%, at least about 20%, at least about 25%, at least about 30%, at least about 35%, at least about 40%, at least about 45%, or at least about 50% lower than the level of SFA in the same food product from a control animal (e.g., a non-transgenic animal of the same species). The level of SFA in a subject food product is lower than the level of SFA in the same food product from a control animal, even without processing. For example, milk from a non-transgenic animal can be treated or processed to have a lower SFA content. However, the SFA content of a subject food product is lower without the need for any processing steps.

The weight percent (e.g., weight percent of the total amount of SFA, MUFA, and PUFA combined) of SFA in a subject food product is from about 10 to about 67.5 weight percent, e.g., from about 65 to about 67.5, from about 60 to about 65, from about 55 to about 60, from about 50 to about 55, from about 45 to about 50, from about 40 to about 45, from about 35 to about 40, from about 30 to about 35, from about 25 to about 30, from about 20 to about 25, from about 15 to about 20, or from about 10 to about 15 weight percent.

Thus, e.g., where the subject food product is milk or a milk-containing product, the proportion (e.g., weight percent of the total amount of SFA, MUFA, and PUFA) of SFA in the milk or milk product is from about 65 to about 67.5, from about 60 to about 65, from about 55 to about 60, from about 50 to about 55, from about 45 to about 50, from about 40 to about 45, from about 35 to about 40, from about 30 to about 35, from about 25 to about 30, from about 20 to about 25, from about 15 to about 20, or from about 10 to about 15 weight percent.

The level of MUFA in a subject food product (e.g., milk, meat, or egg, or a milk-, or meat-, or egg-containing food product) of a subject transgenic animal, is at least about 5%, at least about 10%, at least about 15%, at least about 20%, at least about 25%, at least about 30%, at least about 35%, at least about 40%, at least about 45%, or at least about 50% higher than the level of MUFA in the same food product from a control animal (e.g., a non-transgenic animal of the same species).

Thus, e.g., the weight percent of MUFA in a subject food product is from about 27 to about 80 weight percent, e.g., from about 27 to about 30, from about 30 to about 35, from about 35 to about 40, from about 40 to about 45, from about 45 to about 50, from about 50 to about 55, from about 55 to about 60, from about 60 to about 65, from about 65 to about 70, from about 70 to about 75, or from 75 to about 80 weight percent.

The level of PUFA in a subject food product (e.g., milk, meat, or egg, or a milk-, or meat-, or egg-containing food product) of a subject transgenic animal, is at least about 5%, at least about 10%, at least about 15%, at least about 20%, at least about 25%, at least about 30%, at least about 35%, at least about 40%, at least about 45%, or at least about 50% higher than the level of PUFA in the same food product from a control animal (e.g., a non-transgenic animal of the same species).

The weight percent of PUFA in a subject food product is from about 7.5 to about 25 weight percent, e.g., from about 7.5 to about 10, from about 10 to about 15, from about 15 to about 20, or from about 20 to about 25 weight percent.

The level of conjugated linoleic acid (CLA; C18:2 cis 9 trans 11 fatty acid) in a subject milk or milk product is at least about 10%, at least about 15%, at least about 20%, at least about 25%, at least about 30%, at least about 35%, at least about 40%, at least about 45%, at least about 50%, at least 60%, at least 70%, at least 80%, at least 90%, at least 100% (or two-fold), at least 3-fold, at least 4-fold, at least 5-fold, or more, higher than the level in the milk of a control animal.

For example, the weight percent of CLA (and in particular of rumenic acid) in a subject food product is from about 0.380 to about 5.0 weight percent, e.g., from about 0.380 to about 0.390, from about 0.390 to about 0.400, from about 0.400 to about 0.420, from about 0.420 to about 0.440, from about 0.440 to about 0.460, from about 0.460 to about 0.480, from about 0.480 to about 0.500, from about 0.500 to about 0.525, from about 0.525 to about 0.550, from about 0.550 to about 0.575, from about 0.575 to about 0.600, from about 0.650 to about 0.700, from about 0.700 to about 0.750, from about 0.750 to about 0.800, from about 0.800 to about 0.900, from about 0.900 to about 1.0, from about 1.0 to about 1.5, from about 1.5 to about 2.0, from about 2.0 to about 3.0, from about 3.0 to about 4.0, or from about 4.0 to about 5.0 weight percent.

In some embodiments, the CLA (and in particular rumenic acid) is isolated from the milk of a subject transgenic animal, e.g., a composition comprising from about 5 to about 90 weight percent CLA is derived from the milk of a subject transgenic animal. For example, a composition comprising from about 5 to about 10, from about 10 to about 20, from about 20 to about 30, from about 30 to about 40, from about 40 to about 50, from about 50 to about 60, from about 60 to about 70, from about 70 to about 80, or from about 80 to about 90 weight percent CLA (and in particular of rumenic acid) is prepared from the milk of a subject transgenic animal. The composition may further comprise an excipient such as a buffer or a food-grade carrier. The compositions are useful for adding to food products and nutraceuticals.

In some embodiments, a subject food product has from about 10 to about 67 weight percent SFA, from about 27 to about 80 weight percent MUFA, and from about 7.5 to about 25 weight percent PUFA. In some of these embodiments, the food product includes from about 0.400 to about 50 weight percent CLA (and in particular rumenic acid).

The present invention provides food products, including nutraceutical formulations, that include CLA (and in particular rumenic acid). The term "nutraceutical formulation" refers to a food or part of a food that offers medical and/or health benefits including prevention or treatment of disease. Nutraceutical products range from isolated nutrients, dietary supplements and diets, to genetically engineered designer foods, functional foods, herbal products and processed foods such as cereal, soup and beverages. The term "functional foods," refers to foods that include "any modified food or food ingredients that may provide a health benefit beyond the traditional nutrients it contains."

Nutraceutical formulations of interest include foods for veterinary or human use, including food bars (e.g. cereal bars, breakfast bars, energy bars, nutritional bars); chewing gums; drinks; fortified drinks; drink supplements (e.g., powders to be added to a drink); tablets; and the like.

A subject food product or nutraceutical formulation includes a CLA and at least one additional food-grade component. Suitable components include, but are not limited to, mono- and disaccharides; carbohydrates; proteins; amino acids; fatty acids; lipids; stabilizers; preservatives; flavoring agents; coloring agents; sweeteners; antioxidants, chelators, and carriers; texturants; nutrients; pH adjusters; emulsifiers; stabilizers; milk base solids; edible fibers; and the like. The food component can be isolated from a natural source, or can be synthesized. All components are food-grade components fit for human consumption.

Examples of suitable monosaccharides include sorbitol, mannitol, erythrose, threose, ribose, arabinose, xylose, ribulose, glucose, galactose, mannose, fructose, and sorbose. Non-limiting examples of suitable disaccharides include sucrose, maltose, lactitol, maltitol, maltulose, and lactose.

Suitable carbohydrates include oligosaccharides, polysaccharides, and/or carbohydrate derivatives. As used herein, the term "oligosaccharide" refers to a digestible linear molecule having from 3 to 9 monosaccharide units, wherein the units are covalently connected via glycosidic bonds. As used herein, the term "polysaccharide" refers to a digestible (i.e., capable of metabolism by the human body) macromolecule having greater than 9 monosaccharide units, wherein the units are covalently connected via glycosidic bonds. The polysaccharides may be linear chains or branched. Carbohydrate derivatives, such as a polyhydric alcohol (e.g., glycerol), may also be utilized as a complex carbohydrate herein. As used herein, the term "digestible" in the context of carbohydrates refers to carbohydrate that are capable of metabolism by enzymes produced by the human body. Examples of polysaccharides non-digestible carbohydrates are resistant starches (e.g., raw corn starches) and retro-graded amyloses (e.g., high amylose corn starches). Non-limiting examples carbohydrates include raffinoses, stachyoses, maltotrioses, maltotetraoses, glycogens, amyloses, amylopectins, polydextroses, and maltodextrins.

Suitable fats include, but are not limited to, triglycerides, including short-chain ($C_2$-$C_4$) and long-chain triglycerides ($C_{16}$-$C_{22}$).

Suitable texturants (also referred to as soluble fibers) include, but are not limited to, pectin (high ester, low ester); carrageenan; alginate (e.g., alginic acid, sodium alginate, potassium alginate, calcium alginate); guar gum; locust bean gum; psyllium; xanthan gum; gum arabic; fructo-oligosaccharides; inulin; agar; and functional blends of two or more of the foregoing.

Suitable emulsifiers include, but are not limited to, propylene glycol monostearate (PGMS), sodium stearoyl lactylate (SSL), calcium stearoyl lactylate (CSL), monoglycerides, diglycerides, monodiglycerides, polyglycerol esters, lactic acid esters, polysorbate, sucrose esters, diacetyl tartaric acid esters of mono-diglycerides (DATEM), citric acid esters of monoglycerides (CITREM) and combinations thereof Additional suitable emulsifiers include DIMODAN, including DIMODAN™ B 727 and DIMODAN™ PV, GRINDSTED™ CITREM, GRINDSTED™ GA, GRINDSTED™ PS such as GRINDSTED™ PS 100, GRINDSTED™ PS 200, GRINDSTED™ PS 300, GRINDSTED™ PS 400; RYLO™ (manufactured and distributed by DANISCO CULTOR), including RYLO™ AC, RYLO™ CI, RYLO™ LA, RYLO™ MD, RYLO™ MG, RYLO™ PG, RYLO™ PR, RYLO™ SL, RYLO™ SO, RYLO™ TG; and combinations thereof.

Edible fibers include polysaccharides, oligosaccharides, lignin and associated plant substances. Suitable edible fibers include, but are not limited to, sugar beet fiber, apple fiber, pea fiber, wheat fiber, oat fiber, barley fiber, rye fiber, rice fiber, potato fiber, tomato fiber, other plant non-starch polysaccharide fiber, and combinations thereof.

Suitable flavoring agents include natural and synthetic flavors, "brown flavorings" (e.g., coffee, tea); dairy flavorings; fruit flavors; vanilla flavoring; essences; extracts; oleoresins; juice and drink concentrates; flavor building blocks (e.g., delta lactones, ketones); and the like; and combinations of such flavors. Examples of botanic flavors include, for example, tea (e.g., preferably black and green tea), aloe vera, guarana, ginseng, ginkgo, hawthorn, hibiscus, rose hips, chamomile, peppermint, fennel, ginger, licorice, lotus seed, schizandra, saw palmetto, sarsaparilla, safflower, St. John's Wort, curcuma, cardamom, nutmeg, cassia bark, buchu, cinnamon, jasmine, haw, chrysanthemum, water chestnut, sugar cane, lychee, bamboo shoots, vanilla, coffee, and the like.

Suitable sweeteners include, but are not limited to, alitame; dextrose; fructose; lactilol; polydextrose; xylitol; xylose; aspartame, saccharine, cyclamates, acesulfame K, L-aspartyl-L-phenylalanine lower alkyl ester sweeteners, L-aspartyl-D-alanine amides; L-aspartyl-D-serine amides; L-aspartyl-hydroxymethyl alkane amide sweeteners; L-aspartyl-1-hydroxyethylalkane amide sweeteners; and the like.

Suitable anti-oxidants include, but are not limited to, tocopherols (natural, synthetic); ascorbyl palmitate; gallates; butylated hydroxyanisole (BHA); butylated hydroxytoluene (BHT); tert-butyl hydroquinone (TBHQ); and the like.

Suitable nutrients include vitamins and minerals, including, but not limited to, niacin, thiamin, folic acid, pantothenic acid, biotin, vitamin A, vitamin C, vitamin $B_2$, vitamin $B_3$, vitamin $B_6$, vitamin $B_{12}$, vitamin D, vitamin E, vitamin K, iron, zinc, copper, calcium, phosphorous, iodine, chromium, molybdenum, and fluoride.

Suitable coloring agents include, but are not limited to, FD&C dyes (e.g., yellow #5, blue #2, red #40), FD&C lakes; Riboflavin; β-carotene; natural coloring agents, including, for example, fruit, vegetable, and/or plant extracts such as grape, black currant, aronia, carrot, beetroot, red cabbage, and hibiscus.

Exemplary preservatives include sorbate, benzoate, and polyphosphate preservatives.

Suitable emulsifiers include, but are not limited to, diglycerides; monoglycerides; acetic acid esters of mono- and diglycerides; diacetyl tartaric acid esters of mono- and diglycerides; citric acid esters of mono- and diglycerides; lactic acid esters of mono- and diglycerides; fatty acids; polyglycerol esters of fatty acids; propylene glycol esters of fatty acids; sorbitan monostearates; sorbitan tristearates; sodium stearoyl lactylates; calcium stearoyl lactylates; and the like.

Suitable agents for pH adjustment include organic as well as inorganic edible acids. The acids can be present in their undissociated form or, alternatively, as their respective salts, for example, potassium or sodium hydrogen phosphate, potassium or sodium dihydrogen phosphate salts. Exemplary acids are edible organic acids which include citric acid, malic acid, fumaric acid, adipic acid, phosphoric acid, gluconic acid, tartaric acid, ascorbic acid, acetic acid, phosphoric acid and mixtures thereof.

A CLA (and in particular rumenic acid) is present in the food product/nutraceutical formulation in an amount of from about 0.01% to about 50% by weight, e.g., from about 0.01% to about 0.1%, from about 0.1% to about 0.5%, from about 0.5% to about 1.0%, from about 1.0% to about 2.0%, from about 2.0% to about 5%, from about 5% to about 7%, from about 7% to about 10%, from about 10% to about 15%, from about 15% to about 20%, from about 20% to about 25%, from about 25% to about 30%, from about 30% to about 35%, from about 35% to about 40%, from about 40% to about 45%, or from about 45% to about 50% by weight.

Where the food product is a beverage, the food product generally contains, by volume, more than about 50% water, e.g., from about 50% to about 60%, from about 60% to about 95% water, e.g., from about 60% to about 70%, from about 70% to about 80%, from about 80% to about 90%, or from about 90% to about 95% water.

Where the food product is a bar, the food product generally contains, by volume, less than about 15% water, e.g., from about 2% to about 5%, from about 5% to about 7%, from about 7% to about 10%, from about 10% to about 12%, or from about 12% to about 15% water.

In some embodiments, the food product/nutraceutical is essentially dry, e.g., comprises less than about 5%, water.

Monosaccharides, disaccharides, and complex carbohydrates, if present, are generally present in an amount of from about 0.1% to about 15%, e.g., from about 0.1% to about 1%, from about 1% to about 5%, from about 5% to about 7%, from about 7% to about 10%, or from about 10% to about 15%, by weight each. Soluble fibers, edible fibers, and emulsifiers, if present, are generally present in an amount of from about 0.1% to about 15%, e.g., from about 0.1% to about 1%, from about 1% to about 5%, from about 5% to about 7%, from about 7% to about 10%, or from about 10% to about 15%, by weight each.

Other components discussed above, if present, are present in amounts ranging from about 0.001% to about 5% by weight of the composition.

Research Applications

The subject transgenic animals find use in research, to analyze the effects of stearoyl CoA desaturase synthesis in various tissues. The subject transgenic animals are useful for studying the regulation of fatty acid synthesis. In particular, the subject transgenic animals are useful for studying the regulation of transcription and translation of a stearoyl CoA desaturase gene.

For example, mutations may be introduced into the stearoyl CoA desaturase promoter region to determine the effect of altering expression in a stearoyl CoA desaturase transgenic animal.

Stearoyl CoA desaturase regulatory sequences incorporated into a transgene may be used to identify cis acting sequences required for transcriptional or translational regulation of expression, especially in different tissues or stages of development, and to identify cis acting sequences and trans-acting factors that regulate or mediate expression. Such transcription or translational control regions may be operably linked to a reporter gene or a stearoyl CoA desaturase gene to examine the effects of the regulatory sequences on expression levels and mRNA stability.

The subject transgenic animals are also useful for studying the effects of ingestion of a subject food product derived from a subject transgenic animal on the fatty acid and cholesterol composition of various fluids and tissues of animal fed with a subject food product, or on the effects of CLA on the health of the animal as measured by alterations in immune response and growth. In some embodiments, animals are fed with a diet including subject food product from birth. In other embodiments, animals are fed with a diet including subject food product at some time after birth, e.g., as adult animals. In some embodiment, the animals are susceptible to having high levels of serum cholesterol. In other embodiments, the animals are normal (e.g., have normal levels of serum cholesterol).

For example, animals, such as pigs, are fed ad libidum with a ration of 90% pellets mixed with 10% fat skimmed from the milk of a subject transgenic goat, or a ration of 90% pellets mixed with 10% fat skimmed from the milk of a control, non-transgenic goat. For example, pigs are fed such a diet over a period of time of about 7 days, 2 weeks, 3 weeks, 4 weeks, or longer, from the time they are weaned from an all-milk diet (e.g., when they are about 8 days old). After being fed a diet containing a subject food product for a given period of time, various tissues and fluids, e.g., serum, blood cells, and muscle tissues, are analyzed for fatty acid composition (e.g., SFA, MUFA, and PUFA), and cholesterol.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Generation and Characterization of Transgenic Mice and Goats

Materials and Methods

Constructs

A DNA construct designed to express the rat stearoyl CoA desaturase (SCD) cDNA in the mammary gland under control of the milk protein gene beta-lactoglobulin (Blg) promoter was made by standard DNA cloning techniques. The 5526 base pair (bp) bovine Blg-rat SCD construct (pBlgSCD) consisted of 1216 bp of the bovine Blg promoter (from the EagI site at −954) through untranslated exon 1 and the start codon. The start codon was replaced by a XhoI site and was followed by 1831 bp of bovine Blg DNA from +4 to the ClaI site at 4044 and 1349 bp from the untranslated portion of exon 6 through the SphI site at 7639, including 917 bp of 3' flanking DNA. The 1079 bp rat SCD cDNA containing its own translational start and stop codons was inserted at the XhoI site.

Both transgenic mice and goats were produced with DNA construct pBlgSCD by standard pronuclear microinjection procedures. Briefly, donor females were superovulated, bred and one-cell fertilized zygotes were collected from the oviducts. Zygotes with visible pronuclei were microinjected with approximately 2 pl of the DNA construct at a concentration of 5ng/μl and surviving zygotes were then surgically transferred into the oviducts of synchronized recipient females. Pregnancies were carried to term and all offspring born were screened for the presence of the transgene with construct-specific polymerase chain reaction (PCR) primers. PCR-positive founders were confirmed by Southern blot. The mouse lines used for microinjection were an F1 cross of the C57B1/6 and CBA inbred lines, and the goats used were outbred dairy goats.

Primary transgenic mice and goats were bred to non-transgenic control mice and goats, respectively, of the same genetic background. Non-transgenic female siblings of the F1 and F2 transgenic animals were used as controls.

Results

Milk samples were collected once per mouse per lactation at peak lactation (days 10-12) and analyzed for FA composition by gas chromatography 9GC) using standard methods well known in the art (e.g., DePeters et al. (2001) *J. Dairy Sci.* 84:929-936). The "weight percent" of various fatty acids is the amount of the individual fatty acid(s) as a percent of the total amount of fatty acids in the sample.

We observed significant changes in the amount of one or more fatty acids (FAs) (Table 1), thus indicating that the presence of the SCD transgene could affect milk FA composition.

TABLE 1

Mean weight percent of selected FAs in control and SCD transgenic mouse milk.

| Mouse Line | N | c16:0 | c16:1cis | c18:0 | c18:1cis |
|---|---|---|---|---|---|
| SCD-1 | 8 | 25.76** | 3.08 | 2.74 | 22.77 |
| SCD-2 | 21 | 24.19 | 2.73 | 2.74* | 22.08*** |
| SCD-5 | 14 | 25.21 | 2.58 | 3.04 | 22.01** |
| Control | 26 | 23.41 | 2.68 | 3.11 | 25.82 |

N = number of animals sampled;
*p < 0.05;
**p < 0.01;
***p < 0.001 determined by Two Tailed T-test of Means Transgenic goats generated with the same DNA construct as the mice also showed differences in FA composition. The FA composition of goat milk from five SCD transgenic female founder goats in their first lactation was analyzed by gas chromatography. With pronuclear microinjection, the transgene integrates randomly and in different copy numbers in the genome of each founder animal. This may lead to different levels of expression of the transgene in each founder line. Therefore, each transgenic goat must be considered as representing a unique transgenic line, precluding the combining of the results from the different animals. For these reasons, the data was analyzed by comparing the results from the transgenic animals to the mean plus or minus one and two standard deviations for the same FA ratios for the ten control animals sampled at the same age, parity, and stage of lactation.

The percentage of milk yield that represents total fat and protein, as determined by testing through the California Dairy Herd Improvement Association testing program (DHIA) for the five transgenic founders fell in the same range as the averages of our dairy goat herd for both fat and protein, indicating that expression of the transgene did not change the gross composition of the milk. FA composition was analyzed by comparing the ratios of individual desaturation products to precursors as well as on the total amount of SFA, MUFA and PUFA in individual milk samples from each transgenic goat and the mean of ten contemporary controls. Preliminary data was collected from samples taken at days 7, 14 and 30 after parturition.

Figure 1B:
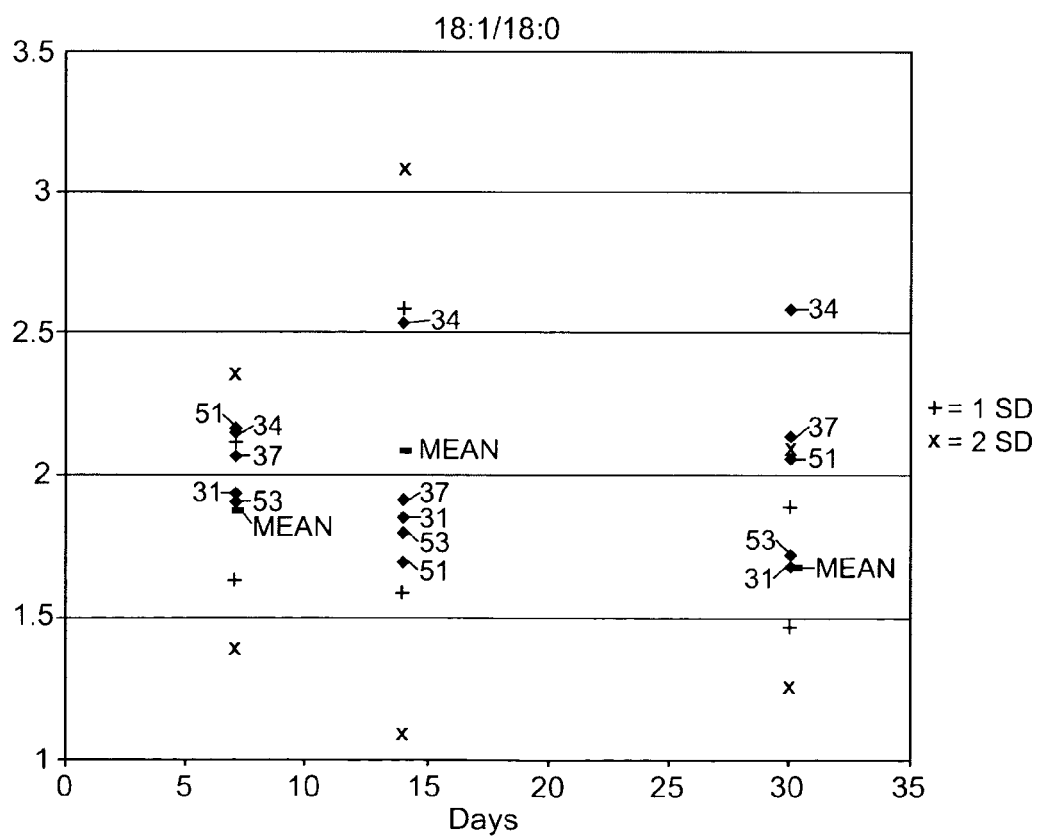
Figure 1C:
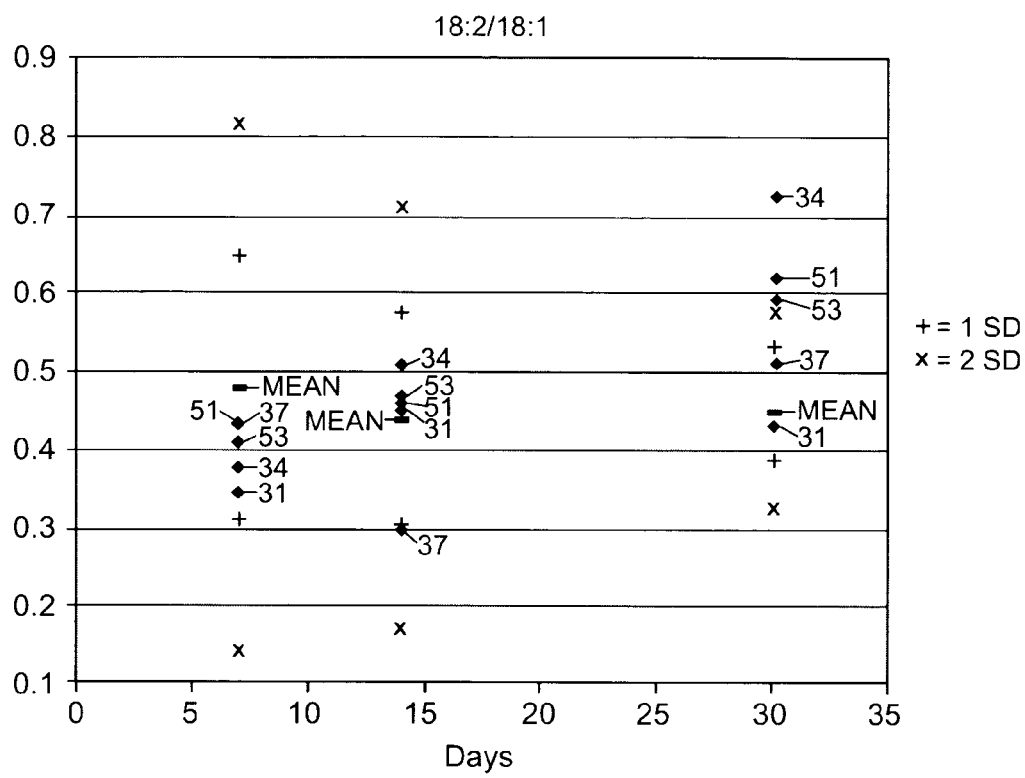

The ratio of 16:1, the 16-carbon MUFA product of SCD, to 16:0, the substrate for this reaction, at days 7 and 14 are higher for two of the five founder animals, thereby indicating increased production of the monounsaturated product. The effect decreased toward control values by day 30 of lactation. The ratio of 18:1, the 18-carbon monounsaturated product of SCD, to 18:0, the substrate, is again greater than (goats 34 and 37) or equal to (goat 51) two standard deviations from the mean of the controls, indicating increased levels of the monounsaturated product (FIG. 1). The ratio of 18:2 cis9trans11, the CLA product of SCD in the mammary gland, to 18:1 trans11, the precursor FA for this reaction, is greater than (goats 34 and 51) or at (goat 53) two standard deviations by day 30 of lactation, indicating increased levels of CLA in the milk of the transgenic goats (FIG. 1).

Figure 2A:
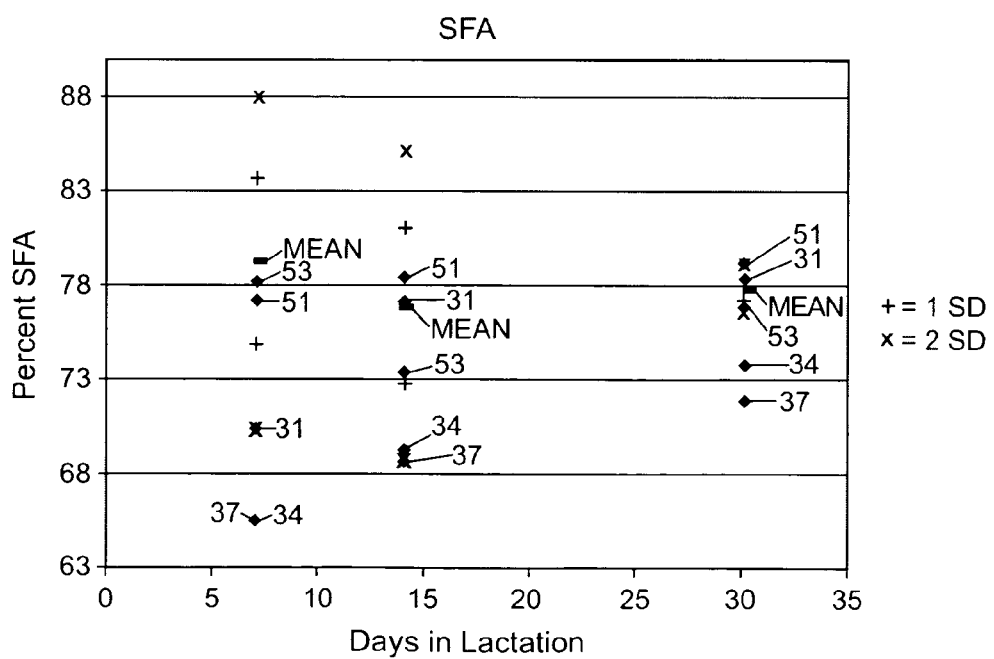

In terms of the total weight percent of SFA, MUFA and PUFA in the milk of the five founder animals, two goats (#34 and #37) consistently have lower overall levels of SFA and higher levels of MUFA than the controls at each of the three time points analyzed (FIG. 2). Goat 34 also has elevated PUFA at all time points, while goats 53 and 37 have a trend towards increasing PUFA levels, which is high by day 30. To date we have obtained transgenic offspring from four of these transgenic goats (#34, 37, 51, 53). Using RT-PCR we have also shown the presence of mRNA specific for the transgene in total RNA isolated from mammary gland epithelial cells sloughed off in the milk of goats 34 and 37.

Reverse transcriptase PCR analysis of mRNA from transgenic desaturase and non-transgenic control goats was carried out. Mammary gland tissue from transgenic and non-transgenic control lactating goats was collected by biopsy. Total RNA was isolated from the tissue by standard procedures, quantified and used for reverse transcriptase PCR. 1 μg of total RNA was treated with DNaseI for 1 hour at 37° C. After heat denaturation, MMLV reverse transcriptase was added and samples were incubated at 40° C. for one hour followed by heat inactivation. 1 µl of each reverse transcriptase reaction was then used for PCR with primers BLG-E1/RSCD4R. These primers are specific for exon 1 of the goat β-lactoglobulin (blg) gene and rat stearoyl CoA (rSCD) desaturase cDNA, respectively. Due to the DNA construct design, the transgenic mRNA should be a fusion message containing the first exon of the goat blg gene fused to the complete cDNA for rSCD. Only transgenic goats should produce a band by RT-PCR with this set of primers. Endogenous message will not be amplified. Results showed that transgenic goats 0034, 0037, 0051 and 0053 express the transgene at the mRNA level while transgenic goat 0031 did not at the time of this assay. As expected, control goats 0281 and 0282 do not show expression. All reaction controls (e.g., RT-PCR without RNA; RT-PCR without reverse transcriptase enzyme) were as expected. These expression results indicate that the changes seen in the fatty acid composition of the milk can be attributed to expression of the transgene.

Example 2

Transgenic Animals Expressing a Stearoyl CoA Desaturase Transgene in Intestinal Epithelial Cells Two DNA constructs are made, which promote expression of the rat SCD cDNA in the small intestine of the mouse under the control of the rat FABPi gene. A 1.2 kb fragment of the rat FABPi promoter from −1179 to +28 is included in the DNA construct. This region of promoter has been shown to promote tissue-specific expression of the human growth hormone gene at levels similar to the endogenous FABP gene (Sweetser et al. supra). The FABPi promoter region is amplified from mouse genomic DNA using a polymerase chain reaction (PCR) with forward primer 5'GAATTCCTTAATTTGCATAA3' (SEQ ID NO:01) from −1179 and reverse primer 5'CTCGAGCAGCTGTGTCATAGTTCT3' (SEQ ID NO:02) from +28. The resulting fragment has an XhoI restriction enzyme site on the 3' end and is cloned into the pGemTEasy vector (Promega). The same rat SCD cDNA with XhoI ends used in Example 1 is then inserted at the unique XhoI site in the above vector. Orientation of the fragment is determined by PCR and verified by sequencing.

A second DNA construct is made with a modified SCD cDNA. The SCD genes have been found to have very long 3' untranslated regions (UTR). These regions have been shown to play a role in message stability and feedback inhibition of expression. A short structural motif of AUUUA (ARE—adenylate/uridylate rich elements) has been implicated as an mRNA destabilizing sequence. The ARE target the mRNA for degradation by acting to bind specific proteins. In adipose tissue, PUFA have been shown to act on SCD message stability. The second DNA construct contains the addition of the 3' UTR region of the rat SCD gene from the stop codon through the polyA sequence (nt 1080-4465) with the five message destabilizing sites AUUUA removed. Fragments are amplified by PCR and cloned into the FABPi vector, or a vector that includes a suitable promoter.

Transgenic mice are generated with both DNA constructs by standard pronuclear microinjection procedures as routinely performed in our laboratory. Briefly, C57B1/6×CBA females are superovulated at 3-4 weeks of age and bred to intact males. One-cell zygotes are collected, microinjected and surgically transferred to synchronous CD1 recipient females. Resulting pups are identified as transgenic by PCR of toe clips taken at 10 days of age. Transgene-specific primers spanning the junction of the FABPi and SCD sequences are used (Forward:5'CACACAGCTGCTCGAGATGG3' (SEQ ID NO:03); Reverse:5° CTCGAGTCAGCTACTCTTGTG3'; (SEQ ID NO:04)). The presence of the transgene is confirmed by Southern blotting with a probe spanning the two sequences. Founder animals are bred to non-transgenic control mice of the same background to establish lines. The level of SCD mRNA is analyzed by Northern blot analysis.

Example 3

Generation of a Transgenic Pig

The following is a non-limiting example of how to make a transgenic pig. Pig embryos are recovered from the oviduct, and are placed into a 1.5 ml microfuge tube containing approximately 0.5 ml embryo transfer media (Beltsville Embryo Culture Medium). Embryos are centrifuged for 12 minutes at 16,000× g RCF (13,450 RPM) in a microcentrifuge. The embryos are then removed from the microcentrifuge tube with a drawn and polished Pasteur pipette and placed into a 35 mm petri dish for examination. If the cytoplasm is still opaque with lipid such that pronuclei are not visible, the embryos are centrifuged again for 15 minutes. Embryos are then placed into a microdrop of media (approximately 100 µl) in the center of the lid of a 100 mm petri dish, and silicone oil is used to cover the microdrop and fill the lid to prevent media from evaporating. The petri dish lid containing the embryos is set onto an inverted microscope equipped with both a heated stage and Hoffman Modulation Contrast optics (200× final magnification). A finely drawn and polished micropipette is used to stabilize the embryos while about 1-2 picoliters of HPLC-purified DNA solution containing approximately 200-500 copies of the transgene construct are delivered into the male or female pronucleus with another finely drawn micropipette. Embryos surviving the microinjection process as judged by morphological observation are loaded into a polypropylene tube (2 mm ID) for transfer into a recipient pig.

The Examples provided above demonstrate that the present invention provides transgenic non-human animals expressing a stearoyl CoA desaturase transgene in milk or the intestine, and that the milk or muscle tissue from such animals has a lower level of saturated fatty acids than the milk or muscle tissue from a non-transgenic littermate.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A non-human transgenic mammal whose genome comprises a transgene comprising a nucleotide sequence encoding a stearoyl coenzyme A desaturase, wherein said desaturase-encoding nucleotide sequence is operably linked to a mammary gland-specific promoter, wherein the transgene is expressed in a mammary gland epithelial cell of said mammal, and wherein said mammal produces milk comprising a level of monounsaturated fatty acids (MUFA) that is at least 5% higher than the level of MUFA in milk produced by a non-transgenic mammal of the same species.

2. The transgenic non-human mammal according to claim 1, wherein said mammal is an ungulate.

3. A method for producing a non-human transgenic mammal of claim 1, said method comprising:
   a) introducing a transgene construct into a single-celled embryo, forming a genetically modified embryo, wherein said transgene construct comprises a nucleotide sequence encoding a stearyl coenzyme A desaturase (SCD), and wherein said SCD-encoding nucleotide sequence is operably linked to a mammary gland-specific promoter;
   b) transferring the genetically modified embryo into a recipient pseudopregnant female of the same species;
   c) allowing said transferred embryo to develop to term; and
   d) identifying a transgenic non-human mammal whose genome comprises the transgene construct, wherein said transgenic non-human mammal produces milk comprising a level of monounsaturated fatty acids (MUFA) that is at least 5% higher than the level of MUFA in milk produced by a non-transgenic mammal of the same species.

4. The method according to claim 3, wherein said transgenic mammal is chosen from a mouse, a rat, a rabbit, a pig, a sheep, a goat, and a cow.

5. The method according to claim 3, wherein said transgene is expressed in mammary gland cells of said mammal.

6. A method of producing a food product, said method comprising harvesting a food product from a non-human transgenic mammal of claim 1, wherein said food product is milk.

7. A method of producing a food product, the method comprising processing a food product harvested from a non-human trans genie mammal of claim 1, wherein said food product is milk.

8. The transgenic mammal of claim 1, wherein said mammal is a female that produces milk comprising a level of polyunsaturated fatty acids (PUFA) that is at least 5% higher than the level of PUFA in milk produced by a non-transgenic mammal of the same species.

9. The transgenic mammal of claim 1, wherein said mammal is a female that produces milk comprising a level of saturated fatty acids (SFA) that is at least 5% lower than the level of SFA in milk produced by a non-transgenic mammal of the same species.

10. The transgenic mammal of claim 1, wherein said mammal chosen from a goat, a cow, and a sheep.

11. The transgenic mammal of claim 1, wherein said mammal is a female that produces milk comprising a level of conjugated linoleic acid (CLA) that is at least 5% higher than the level of CLA in milk produced by a non-transgenic mammal of the same species.

12. The transgenic mammal of claim 1, wherein the mammary gland-specific promoter is a β-lactoglobulin promoter.

13. The trans genie mammal of claim 1, wherein the mammary gland-specific promoter is a β-casein promoter.

14. The transgenic mammal of claim 1, wherein the mammary gland-specific promoter is an αS1-casein promoter.

15. The transgenic mammal of claim 1, wherein the mammary gland-specific promoter is an αS2-casein promoter.

16. The transgenic mammal of claim 1, wherein the mammary gland-specific promoter is a whey acid protein promoter.

* * * * *